(12) United States Patent
Warkentin et al.

(10) Patent No.: US 8,046,064 B2
(45) Date of Patent: Oct. 25, 2011

(54) METHOD OF DELIVERING PESP/ICC AS WELL AS ADJUSTING THE REFRACTORY PERIOD OF THE HEART

(75) Inventors: Dwight H. Warkentin, Arden Hills, MN (US); D. Curtis Deno, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1353 days.

(21) Appl. No.: 11/379,892

(22) Filed: Apr. 24, 2006

(65) Prior Publication Data

US 2007/0250122 A1 Oct. 25, 2007

(51) Int. Cl.
*A61N 1/39* (2006.01)
(52) U.S. Cl. .................................. 607/9; 607/4; 607/14
(58) Field of Classification Search ................ 607/9, 23, 607/17, 4, 5, 6, 14, 15
See application file for complete search history.

(56) References Cited

U.S. PATENT DOCUMENTS

| | | | |
|---|---|---|---|
| 4,945,909 A * | 8/1990 | Fearnot et al. | 607/14 |
| 5,158,078 A | 10/1992 | Bennett et al. | |
| 5,213,098 A | 5/1993 | Bennett et al. | |
| 5,224,475 A | 7/1993 | Berg et al. | |
| 5,226,513 A | 7/1993 | Shibayama | |
| 5,314,448 A | 5/1994 | Kroll et al. | |
| 5,318,593 A | 6/1994 | Duggan | |
| 5,351,687 A | 10/1994 | Kroll et al. | |
| 5,366,485 A | 11/1994 | Kroll et al. | |
| 5,555,888 A | 9/1996 | Brewer et al. | |
| 5,564,434 A | 10/1996 | Halperin et al. | |
| 5,694,943 A | 12/1997 | Brewer et al. | |
| 5,713,924 A | 2/1998 | Min et al. | |
| 5,835,975 A | 11/1998 | Peeters et al. | |
| 6,311,089 B1 | 10/2001 | Mann et al. | |
| 6,587,723 B1 | 7/2003 | Sloman et al. | |
| 6,594,523 B1 | 7/2003 | Levine | |
| 6,738,667 B2 | 5/2004 | Deno et al. | |
| 6,850,795 B2 | 2/2005 | Hoium et al. | |
| 2003/0074029 A1 | 4/2003 | Deno et al. | |
| 2003/0088183 A1 | 5/2003 | Hoium et al. | |

(Continued)

FOREIGN PATENT DOCUMENTS

WO WO03020364 3/2003

(Continued)

OTHER PUBLICATIONS

Brunckhorst et al., "Cardiac Contractility Modulation by Non-Excitatory Currents: Studies in Isolated Cardiac Muscle", The European Journal of Heart Failure, 8. p. 7-15, 2006.

(Continued)

*Primary Examiner* — Carl H Layno
*Assistant Examiner* — Pamela M Bays
(74) *Attorney, Agent, or Firm* — Reed A. Duthler; Stephen W. Bauer (57) ABSTRACT

Medical devices and methods are used to treat cardiac dysfunction conditions which involve delivery of stimulation pulses in cardiac refractory periods in order to modulate an effective refractory period (ERP). Such devices and methods may be used in conjunction with or in place of other therapies, including increased cardiac contractility (ICC) therapy, post extrasystolic potentiation (PESP) therapy, and other therapies to achieve increased heart contractility, provide a safer and more effective regimen for the corresponding stimulation therapies, and reduce the risk of inducing an arrhythmia.

8 Claims, 7 Drawing Sheets

U.S. PATENT DOCUMENTS

| | | | | |
|---|---|---|---|---|
| 2004/0049235 A1* | 3/2004 | Deno et al. | | 607/9 |
| 2004/0102811 A1* | 5/2004 | Schwartz et al. | | 607/5 |
| 2004/0220631 A1* | 11/2004 | Burnes et al. | | 607/9 |
| 2004/0220638 A1 | 11/2004 | Mulligan et al. | | |
| 2005/0038479 A1* | 2/2005 | Deno et al. | | 607/9 |
| 2005/0075673 A1 | 4/2005 | Warkentin et al. | | |
| 2005/0075676 A1 | 4/2005 | Deno et al. | | |
| 2005/0090872 A1 | 4/2005 | Deno et al. | | |

FOREIGN PATENT DOCUMENTS

WO      WO2005035054      4/2005

OTHER PUBLICATIONS

Swerdlow et al., "Summation and Inhibition by Ultrarapid Train Pacing in the Human Ventricle", Circulation, Dallas, TX, v 76, p. 1101-1109, 1987.

* cited by examiner

METHOD OF DELIVERING PESP/ICC AS WELL AS ADJUSTING THE REFRACTORY PERIOD OF THE HEART

BACKGROUND

The present invention relates generally to implantable medical devices. Many embodiments of the invention are directed more particularly to monitoring acute, episodic, or chronic cardiac dysfunction conditions, including heart failure (HF), and/or treating such conditions by providing appropriate therapies.

Congestive heart failure is an extremely serious affliction. Heart failure (HF) is not a specific disease, but rather a compilation of signs and symptoms, all of which are caused by an inability of the heart to appropriately increase cardiac output during exertion. HF may be caused by chronic hypertension, ischemia, tachyarrhythmias, infarct or idiopathic cardiomyopathy. HF has a great impact on the quality of life, as the sympathetic nervous system is placed in a state of hyperexcitablity, leading to a loss of heart rate variability and rate responsive mechanisms in the heart. In turn, the ability of the heart to relax is impaired, resulting in elevated filling pressures, pulmonary congestion, and low exercise tolerance. These are just a few of the side effects.

The treatment of severe cardiac dysfunction and decompensated heart failure may include inotropic drug therapies. Although these therapies may be beneficial in specific settings, they require administration of a drug, often by intravenous route, with systemic side effects and the time-consuming involvement of skilled clinicians. Electrical stimulation therapies are attractive alternatives because implanted or external devices may administer them very shortly after dysfunction appears or worsens and because their actions may be confined to the heart.

Delivering stimulation during the refractory period of the cardiac cycle is a type of therapy generally referred to as increased cardiac contractility (ICC). ICC therapy, used in this manner, has been observed to cause release of catecholamines such as norepinephrine within the tissue of the heart, potentially contributing to an observed increase in contractility of the cardiac tissue, which in turn, results in increased cardiac output, fewer symptoms of heart failure, and improved exertional capacity. Such ICC therapy may also alter calcium influx from the intra-cellular space into the cardiac myocyte, which could increase the amount of calcium available for muscles contraction both directly and through greater SR calcium uptake and subsequent release.

Another type of electrical stimulation can be provided during the nonrefractory period of the cardiac cycle to enhance cardiac function. This type of paired and coupled stimulation of heart tissue results in an additional electrical depolarization and, when appropriately timed, results in post extrasystolic potentiation (PESP). The additional depolarization, coming shortly after a first depolarization, is likely not associated with a sizable mechanical contraction, and results in increased contractility of subsequent cardiac cycles.

As is known, the above-described therapies, ICC and PESP, as well as other therapies, including pacing, cardiac resynchronization therapy (CRT), and defibrillation capability, may be used alone or in certain combinations to treat cardiac dysfunction, including HF. However, designers of prior art systems utilizing such therapies have needed to proceed with caution in order to provide systems that are both safe and effective. Specifically, regimens have been designed to provide one or more of the therapies in a manner that is most beneficial without significant risk of initiating potential arrhythmia. Delivery of electrical stimulation as the heart tissue is becoming non-refractory can trigger a tachyarrhythmia. This is particularly true if multiple high-amplitude pacing pulses are utilized. Therefore, becoming familiar with appropriate timing parameters associated with one or more of these types of therapies has been essential.

What is needed are additional systems and/or methods that utilize the one or more known therapies available for treating cardiac dysfunction, including HF, in manners that further optimize mechanical function or cardiac output, while also further minimizing the limitations of known cardiac dysfunction therapies.

DETAILED DESCRIPTION

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Certain embodiments of the invention may involve medical devices, including diagnostic monitoring equipment, external medical device systems, or implantable medical devices (IMDs), or combinations of such equipment, systems, and devices. Such IMDs may include implantable hemodynamic monitors (IHMs), implantable cardioverter-defibrillators (ICDs), cardiac pacemakers, cardiac resynchronization therapy (CRT) pacing devices, and drug delivery devices. Further, certain embodiments of the invention may involve methods of treating acute, episodic, or chronic cardiac dysfunction conditions, such as heart failure (HF), cardiogenic shock, pulseless electrical activity (PEA), or electromechanical dissociation (EMD), by providing appropriate therapies, including increased cardiac contractility (ICC) and/or post extrasystolic potentiation (PESP).

ICC and/or PESP therapies can involve electrical stimulation pulses being locally or globally delivered to the atrium or ventricles of patients that may be suffering from cardiac dysfunction conditions, including heart failure. In using one or more of these therapies to treat such patients, one generally expects to increase resulting cardiac function (e.g., contractility), including pressures and flows, while decreasing potential of inducing an arrhythmia. In certain embodiments, the above expectations may be more easily met through the incorporation of a mechanism, refractory period stimulation (RPS), resulting in a safer and more effective setting for administration of the therapies (as further detailed herein).

One type of ICC involves a sub-threshold stimulation being applied to cardiac tissue during a refractory period of the cardiac cycle. This type of ICC is thought to affect ion permeabilities across the myocyte membrane through direct electrical influence on the myocyte ion channels or through indirect mechanisms related to the release of neurohormonal modulators such as catecholamine acting on the myocytes. Another type of ICC involves electrical neurostimulation therapies that are directed at sympathetic nerves in the neck, chest, mediastinum, and heart to enhance mechanical function through neurohormonal modulation. Both of these exemplary therapy types are known as ICC therapies because they are not intended to cause cardiac tissue depolarization and can be accomplished with electrode locations and/or stimulation timing that avoid electrically exciting cardiac tissue. Electrodes near the heart deliver one or more ICC pulses within the refractory period of the myocardium. Of course, electrodes that are not in proximity to the heart or those that are, but direct electrical current away from the myocardium may deliver electrical stimuli at various times throughout the cardiac cycle without directly exciting cardiac tissue.

PESP therapy typically involves stimulation being applied to cardiac tissue during a non-refractory period of the cardiac cycle. In turn, this type of stimulation generally results in increased contractility of subsequent cardiac cycles, which is described in detail in commonly assigned U.S. Pat. No. 5,213,098, herein incorporated by reference in relevant part. The '098 patent further discloses PESP being used in a manner that utilizes one or more sensors and signal processing circuitry to control timing parameters (as further detailed herein).

Although beneficial for cardiac function, the delivery of stimulation pulses for PESP, as well as for ICC, must be controlled so as to minimize the risk of inducing an arrhythmia. For example, during absolute refractory period of the cardiac cycle, the ventricles are refractory so that another depolarization will not be induced via delivery of electrical stimulation. However, following this period, the tissue recovers so that another electrical depolarization is possible upon the delivery of electrical stimulation to the cardiac tissue. As such, this "vulnerable period" of the ventricles must be considered when administering ICC and/or PESP therapy. The vulnerable period represents a time period during which an electrical pulse delivered at, or above, a predetermined amplitude has the risk of inducing a VT or VF episode.

The level of enhancement or potentiation resulting from excitatory PESP stimulation therapy is quite dynamic depending on the timing of its delivery. For example, electrical stimulation pulses delivered shortly after the refractory period ends produce strong subsequent contractions, while further delays of the stimulation diminish the amount of potentiation. Further, stimulation too early (i.e., prematurely) results in no additional potentiation at all since the myocardium is refractory. In summary, the low amplitude PESP pulse is essentially "benefit neutral" when restricted to the absolute refractory period, is not without risk for a short period just slightly longer then the refractory period, rises to a maximum benefit shortly after this short period, and finally declines to again become approximately "benefit neutral" for pulses delivered near the intrinsic cycle length.

As discussed with respect to the vulnerable period, the risk of arrhythmia induction is confined to a relatively narrow time interval just slightly longer than the refractory period. In certain embodiments, such a risk can be reduced if single low amplitude PESP pulses are delivered according to delivery lockout rules, as discussed in related patent disclosure identified as U.S. patent application Ser. No. 10/232,792, filed Aug. 28, 2002 by Deno et al. ('792 application) (US 2004/0049235, published Mar. 11, 2004; also WO 03/020364 A2, published Mar. 13, 2003), herein incorporated by reference in relevant part. Additionally, a delivery rule can be included in order to inhibit or lockout ICC and/or PESP therapies when there is risk of diminishing diastole and coronary blood flow and/or reducing the beneficial effect on hemodynamics.

In turn, it should be apparent that stimulation timing with respect to the refractory-nonrefractory period boundary (in an effort to avoid the vulnerable period) has been considered a critical aspect of obtaining the desired response (from ICC and/or PESP) and controlling risks and benefits of therapy delivery. As is detailed in the '792 application, this timing element can be generally determined from a number of electrical and/or mechanical sensor signals to thereby enable safer and more effective stimulation therapies. As further described in the '792 application, again incorporated herein by reference in relevant part, these and further sensors, including sense/pace electrodes, blood pressure sensors, accelerometers, impedance electrodes, flow probes, microphones, sonometric crystals, and metabolic or chemical sensors can be used to detect the onset and severity of cardiac dysfunction, and/or be used for automatically initiating or terminating appropriate therapies, including ICC and/or PESP.

As exemplified in certain embodiments described below, a mechanism, referenced as refractory period stimulation (RPS) can be used in treating conditions of cardiac function. RPS involves one or more stimulation pulses being administered to cardiac tissue during the refractory period for dual purposes: (i) to increase contractility of the cardiac tissue and (ii) to provide modulation of the refractory period. As should be appreciated, since RPS involves stimulation being provided during the refractory period, the therapy, in certain embodiments, can involve a variation of ICC, and as such, can take the place of such ICC therapy. Alternatively, in certain embodiments, RPS can be used in conjunction with one or more of ICC and/or PESP therapies, as well as other therapies for treating cardiac dysfunction. RPS therapy used in this fashion can be generally referenced with respect to one of the therapy's functions, refractory period modulation (RPM). In summary, RPS involves a refractory period stimulation therapy, under which there are at least two applications, one of which includes providing a variation of ICC and another which includes RPM.

RPS can be used in place of ICC, or alternately, used in conjunction with the ICC and/or PESP therapies, as well as other therapies used for treating conditions of cardiac dysfunction. As such, RPS can help achieve a safer and more effective setting for administration of the stimulation pulses, e.g., of the RPS therapy itself and/or of other therapies. In particular, RPS can be used to modulate the refractory period, or effective refractory period (ERP), of the cardiac cycle so as to make it safer and/or easier to avoid the vulnerable period with respect to these stimulation pulses. For example, when used instead of ICC, or alternatively, used in conjunction with ICC therapy, it would often be desirable to elongate the ERP in order to have a bigger "target to hit" with respect to the stimulation pulse distribution. Conversely, when used with PESP therapy, it would often be desirable to shorten the ERP as it is common that the ERP is too long (e.g., in HF patients) to get adequate benefit from the PESP stimulation pulses. As described below, in certain embodiments, RPS could be used to modulate the ERPs accordingly.

RPS builds upon some of the conclusions presented by Swerdlow et al. in their publication, dealing with summation and inhibition of ERP following application of stimulation pulses during the refractory period of the cardiac cycle, herein incorporated by reference in relevant part (see Swerdlow et al., "Summation and Inhibition by Ultrarapid Train Pacing in the Human Ventricle", *Circulation*, Dallas, Tex., v. 76, p. 1101-1109, 1987.). Accordingly, ERP lengths were generally found to decrease in response to higher stimulation pulse amplitudes (inhibition), while ERP lengths were found to increase in response to lower stimulation pulse amplitudes (summation). As such, during times in which therapies are provided to treat conditions of cardiac dysfunction, such as with ICC or PESP therapies, these principles can, in turn, be utilized as further described herein.

It will be appreciated from the following description that the medical devices of embodiments of the invention may be utilized to obtain the aforementioned parameters as stored patient data over a period of time and, in turn, to deliver therapies for treating the cardiac dysfunction conditions, such as heart failure. In certain embodiments, the therapies may include physician involvement. For example, the physician may initiate uplink telemetry of the patient data in order to review it to make an assessment of the heart failure state of the patient's heart. The physician may then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies may include drug therapies and/or electrical stimulation therapies, including RPS, PESP and/or ICC stimulation, and pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and the therapies that are delivered.

Accordingly, in certain embodiments, a multi-chamber pacing system may be modified to derive the aforementioned parameters indicative of cardiac mechanical dysfunction from sensors, sense electrodes, and electrical stimulation electrodes located in operative relation to one or more heart chambers. In turn, such a system may be programmed to operate as an AV sequential, bi-atrial, or bi-ventricular pacing system operating in demand, atrial tracking, and triggered pacing for restoring synchrony in depolarizations and contraction of left and right ventricles in synchronization with atrial sensed and paced events for treating ailments, e.g., HF and/or bradycardia. In certain embodiments, such a system may be programmable to operate as a two, three, or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described above can be selectively programmed to function as or be physically incorporated into a simpler, single chamber, monitoring/stimulation system for deriving the parameters indicative of heart failure state and delivering a sub-set of the aforementioned therapies.

Figure 1:
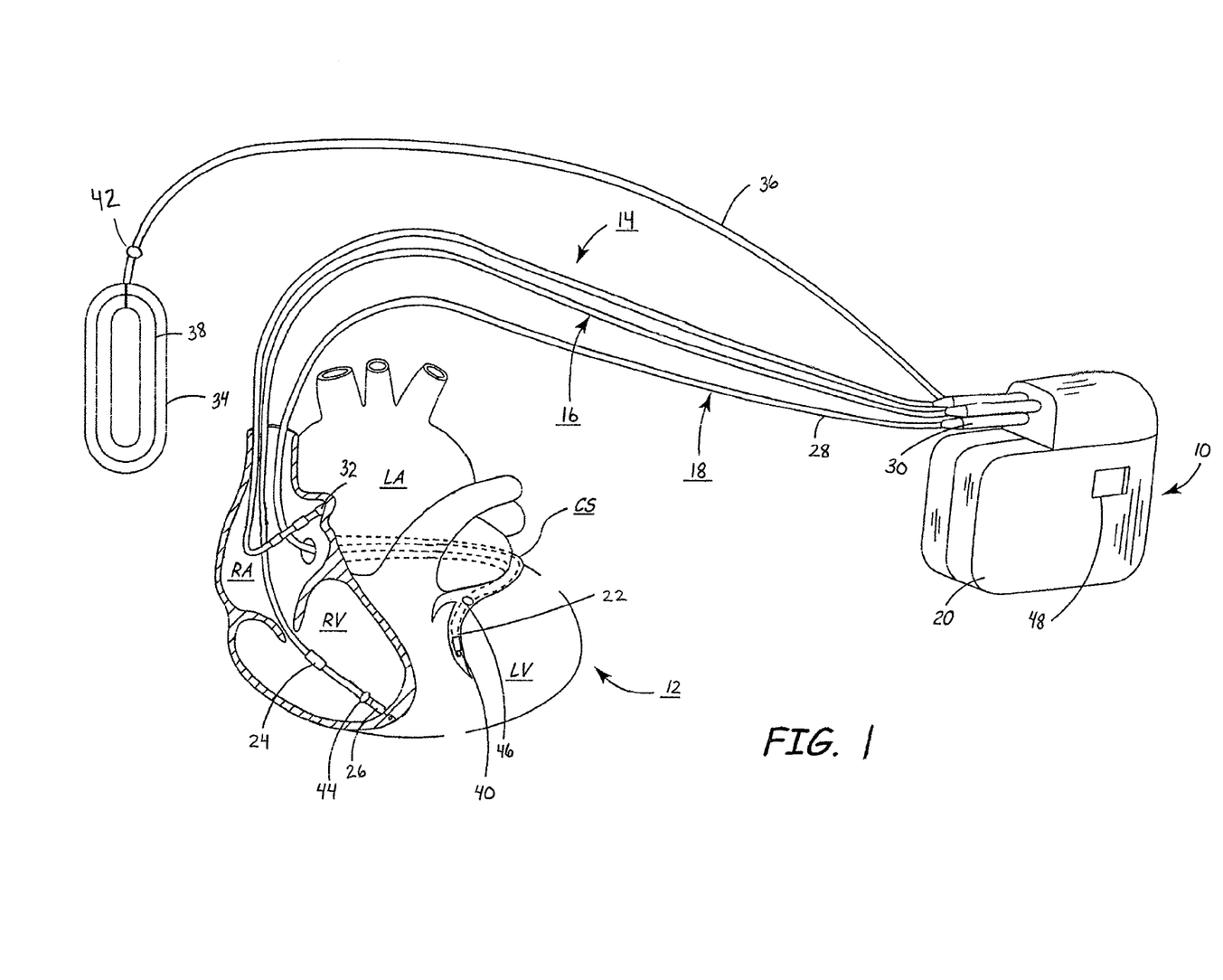
FIG. 1 is a schematic diagram depicting a multi-channel, atrial and bi-ventricular, monitoring/pacing IMD in which embodiments of the invention is preferably implemented.

FIG. 1 is a schematic representation of an IMD 10 that may be used in accordance with embodiments of the invention. The IMD 10 may be any device capable of measuring hemodynamic parameters (e.g., blood pressure signals) from within a patient's heart and/or other cardiac signals, such as the patient's electrogram (EGM). In FIG. 1, heart 12 includes right atrium (RA), left atrium (LA), right ventricle (RV), left ventricle (LV), and coronary sinus (CS) extending from the opening in the RA laterally around the atria to form the great vein.

In FIG. 1, the IMD 10 is depicted in relation to the heart 12. In certain embodiments, the IMD 10 may be an implantable, multi-channel cardiac pacemaker that may be used for restoring AV synchronous contractions of the atrial and ventricular chambers and simultaneous or sequential pacing of the heart ventricles. The IMD 10 is generally implanted subcutaneously in a patient's body between the skin and the ribs. In certain embodiments, as shown, three endocardial leads 14, 16 and 18 are used, respectively connecting the IMD 10 with the RA, the RV, and the LV. Each lead includes at least one electrical conductor and corresponding pace/sense electrode. A remote can electrode 20 may be formed as part of the outer housing surface of the IMD 10. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover, other leads and pace/sense electrodes may be used instead of those depicted. As noted above, the IMD 10 may alternatively be an implantable cardioverter defibrillator (ICD), a cardiac resynchronization therapy (CRT) device, an implantable hemodynamic monitor (IHM), or any other such device or combination of devices, according to various embodiments of the invention.

In certain embodiments, distal LV CS active pace/sense electrode 22 of the lead 18 is paired with proximal RV defibrillation coil 24 or the can 20 for delivering LV pace pulses. The distal LV CS active pace/sense electrode 22 is also preferably paired with the distal tip RV active pace/sense electrode 26 for sensing across the RV and LV. Moreover, in a four-chamber embodiment, the LV CS lead 18 could also bear a proximal LA CS pace/sense electrode along its lead body 28 to lay in the larger diameter CS adjacent the LA. In that case, the lead body 28 would encase two electrically insulated lead conductors extending proximally from the more proximal LA CS pace/sense electrode(s) and terminating in a bipolar connector 30. The lead body 28 may also be smaller between the proximal LA CS electrode and the distal LV CS active pace/sense electrode 22. RA pacing and sensing can occur between electrode 32 and housing 20.

Typically, in pacing systems of the type illustrated in FIG. 1, the electrodes designated herein as "pace/sense" electrodes are used for both pacing and sensing. In certain embodiments, these electrodes can be used exclusively as pace or sense electrodes or used in common as pace/sense electrodes in programmed combinations for sensing cardiac signals and delivering pace pulses along pacing and sensing vectors. However, in other certain embodiments, one or more of the leads shown in FIG. 1 may carry one or more sensors, including pressure sensors for measuring systolic and diastolic pressures and/or a series of spaced apart impedance sensing leads for deriving volumetric measurements of the expansion and contraction of the RA, LA, RV and LV.

In certain embodiments, a subcutaneous electrode 34 coupled to medical electrical lead 36 may be added to or substituted for one or more of the leads/electrodes depicted in FIG. 1. If electrode 34 is used, a suitable defibrillation coil 38 may be coupled to high voltage circuitry to deliver a defibrillation pulse. Also, while coil electrode 24 is shown as being coupled to a portion of RV lead 16, such an electrode may be coupled to portions of any of the leads of FIG. 1, such as LV electrode 40. The coil electrode 24, the subcutaneous electrode 34, or other electrode types may be electrically coupled to low voltage circuitry in addition to high voltage circuitry. As is known, such electrodes may be disposed in a variety of locations in, around, and on the heart.

FIG. 1 also depicts an SQ sensor 42, an RV sensor 44 and an LV sensor 46, which may comprise one or more of a variety of sensors as known in the art. Preferably, RV sensor 44 comprises an absolute pressure sensor, but other pressure sensors may be utilized. Also, RV sensor 44 and SQ sensor 42 may comprise an accelerometer, impedance electrode, saturated oxygen sensor, pH sensor, and the like. In addition, each of the leads can carry a mechanical sensor for developing systolic and diastolic pressures and a series of spaced apart impedance sensors for developing volumetric measurements of the expansion and contraction of the RA, LA, RV, and LV.

Of course, such sensors must be rendered biocompatible and reliable for long-term use. With respect to embodiments involving delivery of ICC therapy, the preferred location for at least one electrode is within the heart, proximite to the myocardial tissue. In addition, one or more sensors may be disposed in or on the housing 20 of IMD 10. While all the components of the system of FIG. 1 are not referenced and described in detail herein, it should be appreciated that such are generally commonplace to such systems, and as such, should be known to those skilled in the art.

According to certain embodiments of the invention, a system constructed and operated to deliver the therapies exemplified herein may include a signal generator, a timing circuit, and/or a microprocessor control circuit of the types generally included in existing pacemaker or ICD systems as are known in the art. Exemplary systems are shown in U.S. Pat. Nos. 5,158,078, 5,318,593, 5,226,513, 5,314,448, 5,366,485, 5,713,924, 5,224,475 and 5,835,975, each of which is incorporated herein by reference in relevant part, although any other type of pacing and/or ICD system similarly constructed may be referenced as well.

The most fundamental sensors in such systems are those based on electrograms (ECGs or EGMs), which reflect cardiac electrical activity. These sensors require electrodes to be located where they can readily detect depolarization and repolarization signals as well as sense amplifiers for the monitoring of heart rhythm and diagnosis of arrhythmias. Such electrodes may be carried on leads placed within the chambers of the heart, and/or on the housing of the device. Alternatively, subcutaneous (SQ) and/or external pad or patch electrodes may be used to sense cardiac signals. Physiologic sensors may likewise be carried on device housings lead or SQ systems according to any of the configurations and/or sensing systems known in the art.

Figure 2A:
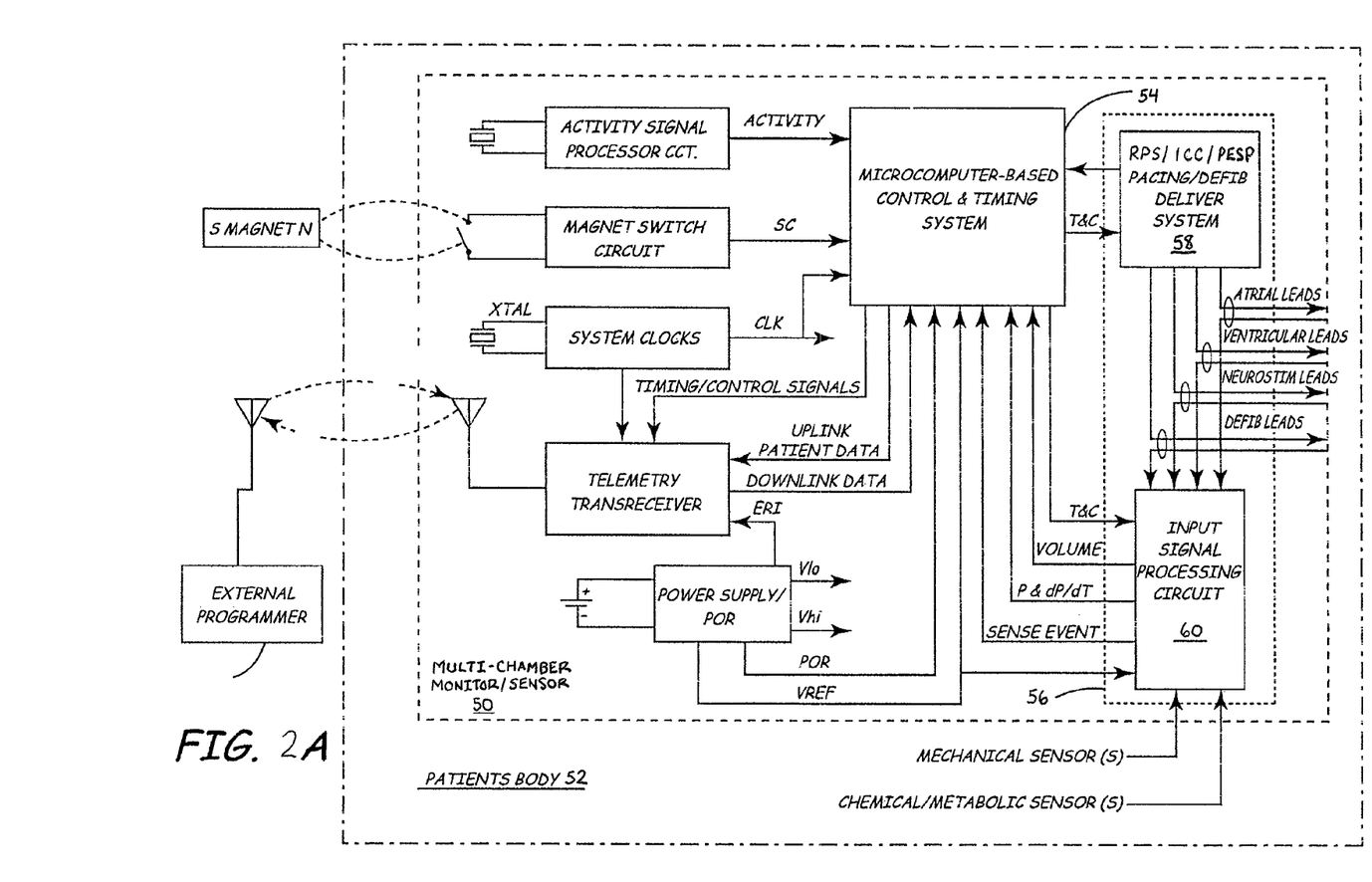
FIG. 2A is a simplified block diagram of one embodiment of circuitry and associated leads employed in the system of FIG. 1 enabling selective therapy delivery and heart failure state monitoring in one or more heart chambers.

FIG. 2A depicts system architecture of exemplary multi-chamber monitor/sensor 50 implanted in a patient's body 52 which provides delivery of a therapy and/or physiologic input signal processing. As is known, the typical multi-chamber monitor/sensor 50 has a system architecture constructed about a microcomputer-based control and timing system 54 which varies in sophistication and complexity based on the type and functional features incorporated therein.

The monitor/sensor 50 also typically includes patient interface circuitry 56 for receiving signals from sensors and/or pace/sense electrodes located at sites of the patient's heart chambers. In certain embodiments, the patient interface circuitry 56 may be equipped to deliver RPS, ICC, PESP, or other stimulation to derive heart failure parameters or to provide therapy to the heart chambers. As shown, patient interface circuitry 56 includes a RPS/ICC/PESP/PACING/DEFIB therapy delivery system 58, optionally including pacing and other stimulation therapies, and a physiologic input signal processing circuit 108 for processing the blood pressure and volumetric signals output by sensors. In certain embodiments, as shown, a set of lead connections are provided for making electrical connections between the therapy delivery system 58 and an input signal processing circuit 60 and sets of pace/sense electrodes located in operative relation to the RA, LA, RV and LV. Alternatively, the therapy delivery system 58 can be configured as a drug pump for delivering drugs into the heart to alleviate heart failure or to operate an implantable heart assist device or pump implanted in patients awaiting a heart transplant operation.

As depicted in FIG. 2A, chemical/metabolic sensor input and/or mechanical sensor inputs are provided to the input signal processing circuit 60. As described with respect to FIG. 1, a wide variety of such sensors may be utilized when practicing embodiments of the invention.

In order for the exemplary circuit of FIG. 2A to implement RPS, ICC, PESP, pacing, or cardiac defibrillation therapy accordingly, the therapy delivery system 58 needs to utilize appropriate circuitry. For example, if an ICC electrode is disposed remotely from the heart, the delivery of ICC therapy may occur independent of the cardiac cycle (e.g., periodically approximately between 10 ms and about 10 seconds). While many different types of pulses may be employed for ICC therapy, one or more pulses of about 0.1 to about 10 ms duration generally have been found to provide the desired results. Effective ICC therapy may be delivered using a variety of electrode configurations (e.g., between one and several discrete electrodes). Also, standard tip, ring, coil, can, and subcutaneous electrodes may be utilized to effectively deliver ICC therapy. While not specifically depicted in the drawings, suitable external circuitry may be adapted for ICC therapy delivery including use of surface electrode patches, pads or paddles as well as pericardial electrodes. In particular, one or more electrodes disposed in the pericardial sac will be well positioned to stimulate cardiac tissue and the sympathetic nerves.

The physiologic input signal processing circuit 60 includes at least one electrical signal amplifier circuit for amplifying, processing, and in some cases, detecting sense events from the electrical sense signal or sensor output signal. The physiologic input signal processing circuit 60 in multi-chamber monitor/sensors providing dual chamber, multi-site, or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 54 for sampling, digitizing, and storing or transmitting in an uplink transmission. Atrial and ventricular sense amplifiers include signal processing stages for respectively detecting the occurrence of a P-wave or R-wave and providing an A-SENSE or V-SENSE event signal to the control and timing system 54. The timing and control system 54 responds in accordance with its operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal-processing channel for sensing and processing a sensor-derived signal from a physiologic sensor located in relation to a heart chamber or elsewhere in the body.

Figure 2B:
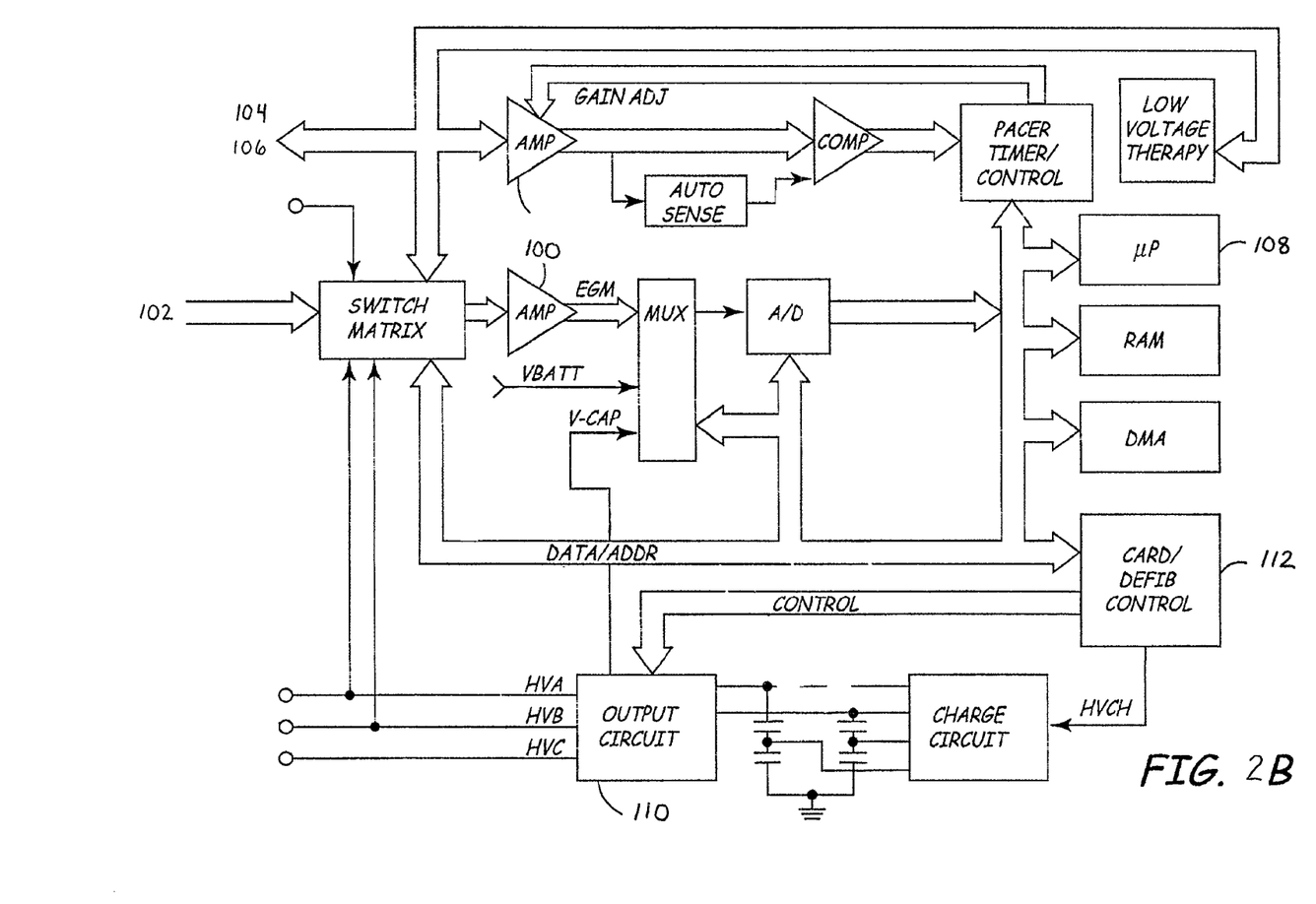
FIG. 2B is a simplified block diagram of a further embodiment of circuitry and associated leads employed in the system of FIG. 1 enabling selective therapy delivery and heart failure state monitoring in one or more heart chambers.

Now turning to FIG. 2B, another system architecture for use in conjunction with embodiments of the invention is depicted. FIG. 2B is an exemplary system that may be utilized to deliver therapy by incorporating the system and method described herein. The system includes a sense amplifier 100 to sense electrical signals, e.g., EGM signals, using one or more leads placed within a respective chamber of the heart. These signals are used to determine atrial and ventricular depolarizations and Q-T length so that ICC and PESP delivery is provided in an optimized manner. One or more physiologic or hemodynamic signals may be sensed using sensors such as those discussed above. These additional signals, shown collectively on line 102, may be used to determine cardiac output so that therapy may be initiated, terminated, and/or optimized.

The system further includes a timer/controller to control the delivery of pacing pulses on output lines 104 and 106. This circuit, alone or in conjunction with microprocessor 108, controls interval lengths, pulse amplitudes, pulse lengths, and other waveform attributes associated with RPS, ICC, PESP, and other therapy pulses. Output circuit 110 delivers high-voltage stimulation such as defibrillation shocks under the control of defibrillation control circuit 112.

Not all of the conventional interconnections are shown in either FIG. 2A or FIG. 2B and many other variations on the illustrated electronic circuitry are possible, as is known to those of skill in the art. In addition, while all the mechanical and electrical components of the systems shown in FIGS. 2A and 2B are not referenced or described in detail, such are generally common to such systems, and as such, should be known to those skilled in the art.

Figure 3:
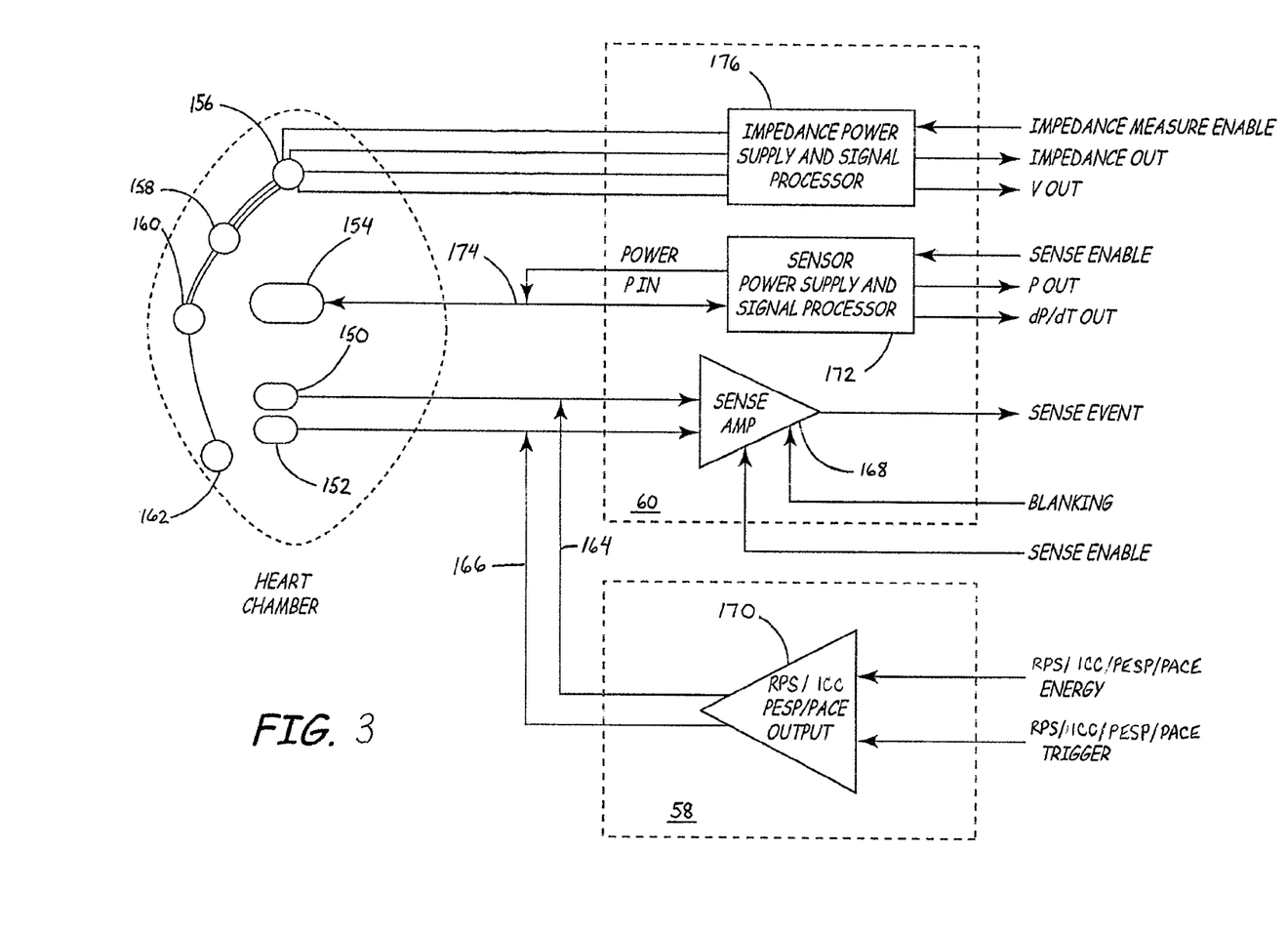
FIG. 3 is a simplified block diagram of a single monitoring and pacing channel for deriving pressure, impedance and cardiac EGM signals employed in monitoring HF and optionally pacing the heart and delivering therapy in accordance with embodiments of the invention.

FIG. 3 schematically illustrates one pacing, sensing, and parameter measuring channel in relation to one heart chamber. Pace/sense electrodes 150, 152, a sensor 154 (e.g., a pressure, saturated oxygen, flow, pH or the like), and a plurality, e.g., four, of impedance-measuring electrodes 156, 158, 160, 162 are located in operative relation to the heart chamber. The pace/sense electrodes 150, 152 are located in operative relation to the heart chamber and are each coupled through lead conductors to the inputs of a sense amplifier 168 located within the input signal processing circuit 60. The sense amplifier 168 is selectively enabled by the presence of a sense enable signal that is provided by control and timing system (not included in FIG. 3, but referenced in FIG. 2A as 54). The sense amplifier 168 is enabled during prescribed times when pacing is either enabled or not enabled in reference to the measurement of the parameters of heart failure. A blanking signal is provided by control and timing system upon delivery of a RPS, ICC, PESP, or other therapy pulse/pulse train to disconnect the sense amplifier inputs from the lead conductors 164 and 166 for a short blanking period in a manner well known in the art.

The pace/sense electrodes 150, 152 are also respectively coupled through lead conductors 164 and 166 to the output of a pulse generator 170. In certain embodiments, the pulse generator 170, within the therapy delivery system 58, selectively provides a pacing pulse to electrodes 150, 152 in response to a RPS/ICC/PESP/PACE trigger signal generated at a time-out of an escape interval (EI) timer within control and timing system in a manner well known in the pacing art or, alternatively, in the manner described in the above-referenced '098 patent to cause the heart chamber to contract more forcefully, the increased force depending upon the duration of the EI.

The sensor 154 and any other physiologic sensors are coupled to a sensor power supply and signal processor 172 within the input signal processing circuit 60 through a set of lead conductors 174 that convey power to the sensor 154 and sampled blood pressure P signals from the sensor 154 to the sensor power supply and signal processor 172. The sensor 154 and a sensor power supply and signal processor 172 may take the form and functionality disclosed in commonly assigned U.S. Pat. No. 5,564,434, herein incorporated by reference in relevant part.

A variety of hemodynamic parameters may be recorded, for example, including RV systolic and RV diastolic pressures, estimated pulmonary artery diastolic pressure (ePAD), pressure changes with respect to time (dP/dt), heart rate, activity, and temperature. Some parameters may be derived from others. For example, the ePAD parameter may be derived from RV pressures at the moment of pulmonary valve opening, and heart rate may be derived from an EGM recording.

The impedance electrodes 156, 158, 160, and 162 are each coupled by a lead conductor to the impedance power supply and signal processor 178. Impedance-based measurements of cardiac parameters such as stroke volume are known as having an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. One or more of the impedance leads may be combined with the pace/sense and/or pressure sensor bearing lead.

A measure of heart chamber volume V can be provided by the set of impedance electrodes 156, 158, 160, and 162 when the impedance power supply and signal processor 176 is enabled by an impedance measure enable signal provided by control and timing system 54.

Figure 4:
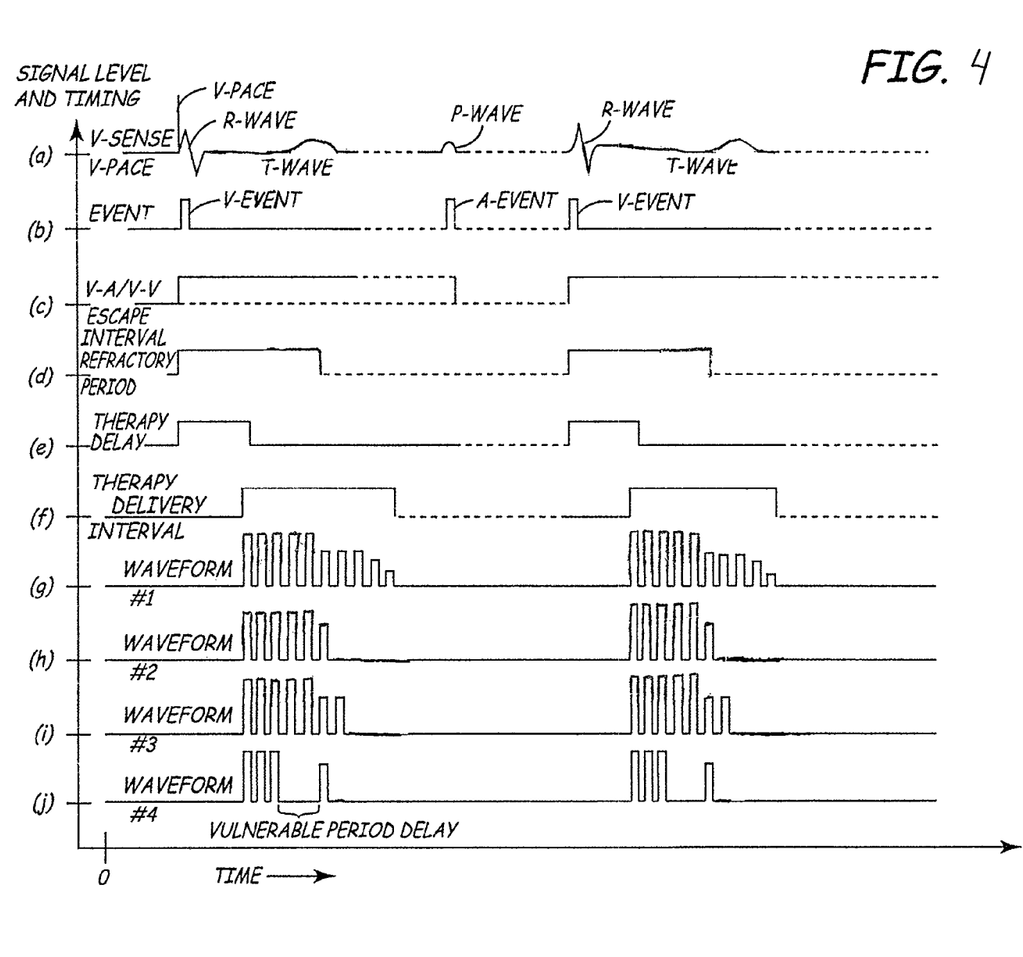
FIG. 4 depicts the delivery of therapeutic stimulation, particularly, pacing energy pulse trains commenced during the refractory period of the heart and continuing for a delivery interval.

Turning to FIG. 4, the exemplary timing diagram shown illustrates the timing of delivery of PESP and ICC stimulation in relation to a timed interval from a sensed or paced event as well as alternative pulse waveforms of the PESP and ICC stimulation. In accordance with one aspect of embodiments of the invention, a therapeutic stimulation delay illustrated in tracing (e) is timed out from a sensed or paced event (e.g., the illustrated V-EVENTs) that for ICC starts with the sensed or paced event and is shorter than the refractory period of the heart. An ICC stimulus pulse train is delivered to the ventricles in the depicted therapy delivery interval of tracing (f) commencing after time-out of the delay and before the end of the refractory period so that the delivery of the ICC therapy falls within the refractory period. The pulses for PESP therapy delivery are intended to be supra-threshold in nature, and therefore must be of sufficient energy to depolarize the heart when they are delivered in the non-refractory period of the heart cycle so that the heart is captured by at least one of the PESP pulses falling outside the refractory period. For simplicity of illustration, the tracings (f)-(j) are expanded in length, and the depolarization of the heart that they cause is not depicted in tracing (a). The amplitude and number of ICC pulses and PESP pulses in each therapy pulse train and the spacing between the pulses may also differ from the illustrated tracings (g)-(j).

The ventricular sense or pace event detected in tracing (b) also triggers the timing out of an escape interval in tracing (c) which may be terminated by the sensing of a subsequent atrial or ventricular event, depending on the operating mode of the system. The first depicted sequence in FIG. 4 shows the full time-out of the escape interval in tracing (c), the refractory period in tracing (d), and the therapy delay and delivery intervals in tracings (e) and (f). The therapy delay and therapy delivery intervals can be derived as a function of an intrinsic V-V or V-A escape interval derived by measuring and averaging intervals between intrinsic ventricular and/or atrial sense events or paced events. The therapy delay can also be determined from a measurement of the Q-T interval and by sensor feedback (e.g. accelerometer or pressure) telling when capture occurred. As illustrated, the therapy delay in tracing (e) delays delivery of the therapy pulse train until the QRS complex ends or about 40-60 ms after the V-EVENT well before the start of the vulnerable period of the heart which occurs near the end of the T-wave. The therapy delivery interval is timed to start any time after the V-event and end well before the end of the previously derived V-V or V-A escape interval. In this example, it is extended for ease of illustration of the pulse trains in tracings (f)-(j). The therapy delivery interval can be broken into ICC and PESP therapy delivery intervals, separated by the end of the refractory period.

The therapy stimulation energy is delivered in the form of a burst of one or more constant or variable energy stimulation pulses separated by a pulse separation interval between each pulse of the burst and spanning in time through the therapy delivery interval. All of the pulses can have the same amplitude and energy as shown in waveform 3 of tracing (i). Alternatively, the leading and/or trailing pulses of the pulse train can have ramped amplitudes similar to the waveform 1 illustrated in tracing (g). In tracing (g), the ramp down trailing edge amplitudes of a further sub-set of the pulses of the burst is shown decreasing from the maximum amplitude to terminating amplitude. This embodiment would allow for delivery of higher energy ICC pulses when the tissue is known to be refractory, followed by delivery of progressively lower energy pulses (that may still be producing ICC effects) as the refractory period nears (and arrhythmia induction risk increases). Ultimately, one of the pulses will capture the heart once the refractory period ends, at which point the therapy pulses would be stopped. This would result in continuous ICC therapy delivery until the earliest possible PESP pulse is evoked.

The initial set of ICC pulses delivered during the refractory period can have a higher pulse amplitude or width as shown in the waveforms. The high-energy pulses delivered during the refractory period can enhance potentiation during subsequent heart cycles. Tracing (j) also illustrates alternative numbers and spacing of the pulses of the pulse train, and it will be understood that this embodiment can also employ one or more pulses on either side of the delay.

In addition, it may be desirable to avoid delivering any therapy pulses in the vulnerable period of the heart near the end of the T-wave, particularly if high energy pulses are delivered during the refractory period. Tracing (j) also illustrates a vulnerable period delay between the high energy ICC pulses delivered during the refractory period and the lower energy PESP pulses after the refractory period to avoid delivering any pulses during the vulnerable period of the heart. It would also be possible to lower the pulse energy of the pulses delivered later in the refractory period. Tracing (i) of waveform 3 also shows the PESP therapy being halted due to a sensed event.

The therapy delivery capability is preferably implemented into a system that may include conventional operating modes for pacing and CRT (cardiac resynchronization therapy) therapies as well as cardioversion/defibrillation capabilities or as a stand alone system for simply providing pulse therapies to effect potentiation of myocardial cells between sensed PQRST complexes shown in FIG. 4.

Figure 5:
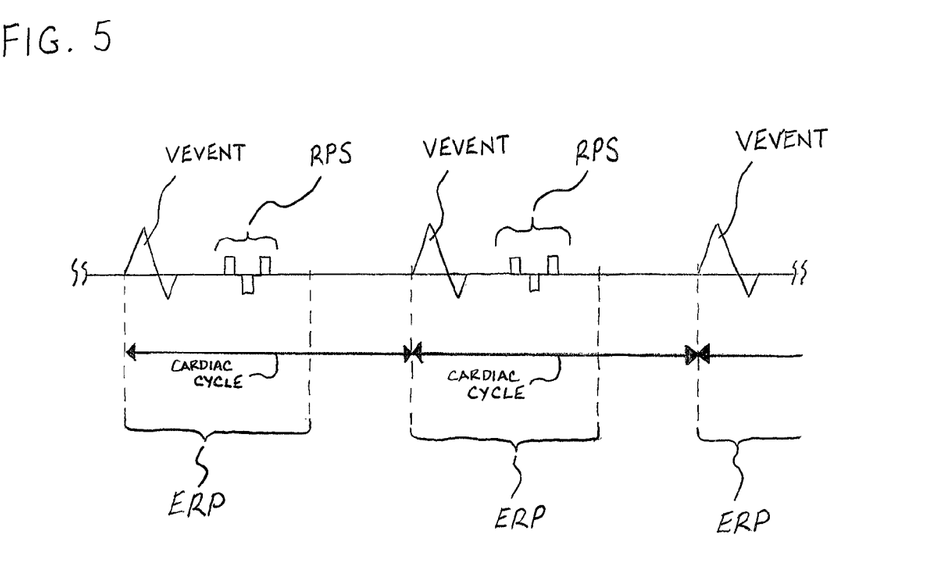
FIG. 5 is an exemplary timing diagram showing the delivery of refractory period stimulation (RPS) used in place of ICC therapy, or alternatively, used in conjunction with ICC therapy in accordance with embodiments of the invention.

FIG. 5 illustrates an exemplary timing diagram that helps depict the delivery of refractory period stimulation (RPS) when used either in place of ICC, or alternatively, in conjunction with ICC therapy in accordance with certain embodiments of the invention. For the sake of simplicity, for embodiments in which the RPS is used in conjunction with the ICC therapy, such ICC pulses are not referenced in FIG. 5; however, it should be appreciated how such pulses may be generally provided for each V-EVENT, as shown in FIG. 4. In accordance with one aspect of embodiments of the invention, RPS delivery is timed out from each sensed or paced event (e.g., the illustrated V-EVENTs), beginning after the sensed or paced event yet terminating prior to the end of the ERP. In certain embodiments, as shown, an RPS administration may include one or more pulses. While RPS is shown to occur a somewhat sizable period of time after each of the V-EVENTs, such is generally shown for clarity to the reader. It is to be realized that the RPS delivery should begin almost immediately after the V-EVENT is sensed, and in certain embodiments, would occur during the V-EVENT. In certain embodiments, RPS may occur at least 30 ms after the beginning of each V-EVENT; however, the invention should not be limited to such.

As further shown in FIG. 5, RPS delivery occurs well within the ERF so as not to induce an arrhythmia. As mentioned above, in certain embodiments, one or more parameters of the RPS may be adjusted periodically in order to modulate the ERP. In accordance with the findings of Swerdlow et al. described above, and in certain embodiments, one of these parameters may be pulse amplitude. In summary, by administering pulses of lower amplitude (e.g., from a predetermined baseline stimulation pulse for the patient) using RPS, one will see an elongation of the ERP almost immediately and within subsequent cycles. In certain embodiments, the therapy delivery system (for example, system 106 in FIG. 2A) may enable an RPS pulse to include voltages of up to about 8 volts. As should be appreciated, modulation of the ERP in the above-described manner would be desirable when RPS is used in place of ICC, or alternatively, used in conjunction with ICC therapy, so that the stimulation pulses can be effectively delivered within the refractory period. In turn, through such EPR modulation (elongation of the EPR), an environment is created where it is easier to position the RPS pulses within such elongated ERP. In addition, when used in conjunction with ICC therapy, one can further minimize any risk of potentially missing the ERP with the ICC stimulation pulses during such therapy, creating a safer mode of providing ICC therapy. As should be appreciated, if the ERP is increased too significantly via RPS, the ERP length can be shortened by increasing the amplitude of the one or more RPS pulses. Therefore, in certain embodiments, one or more parameters of RPS may be monitored so as to be adjusted when necessary in order to "zero in" on the ERP length that is most desired, based on the therapy given (e.g., RPS and/or ICC and/or PESP).

As described above, by being able to modulate the ERP using RPS, ICC therapy, provided in conjunction with RPS, can be made safer and easier. In addition, through the use of RPS in place of ICC, or alternatively, in conjunction with ICC, more energy is applied accordingly to the heart tissue during the refractory period in comparison with ICC being administered solely. Such increased energy generally leads to increased contractility of the corresponding heart tissue, which is one of the goals of ICC therapy. As such, the delivery of RPS at least leads to dual benefits: enabling manipulation of the ERP and increasing contractility of the heart tissue. One method from which contractility can be measured is through examination of hemodynamic parameters, including blood pressure parameters. A detailed discussion of this method of measuring and assessing contractility is provided in U.S. patent application Ser. No. 10/426,425, filed Apr. 30, 2003 by Mulligan et al. ('425 application) (US 2004/0220638 A1, published Nov. 4, 2004), herein incorporated by reference in relevant part.

Figure 6:
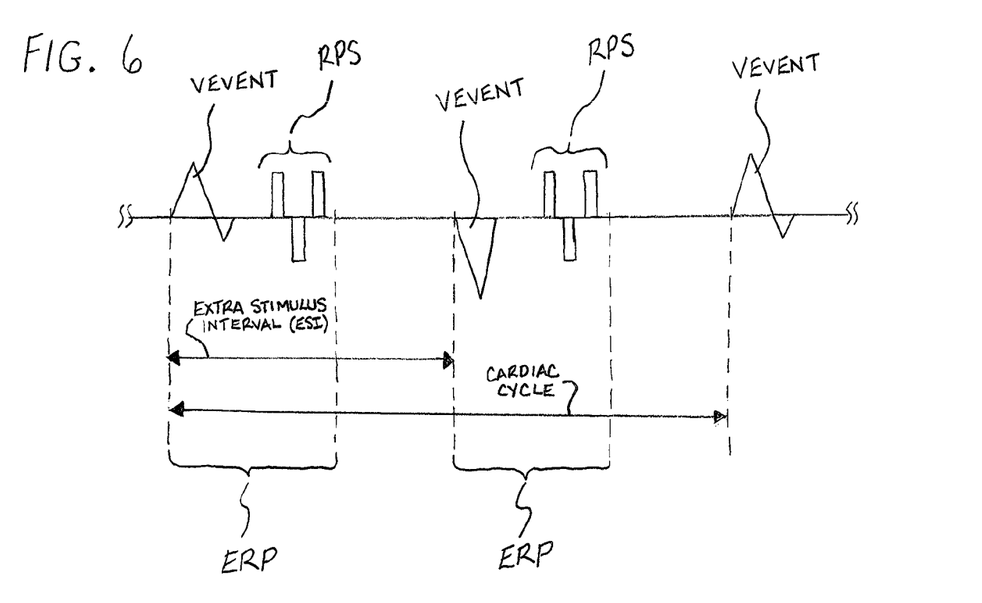
FIG. 6 is an exemplary timing diagram showing the delivery of refractory period stimulation (RPS) during the course of PESP therapy in accordance with embodiments of the invention.

As shown in FIG. 5 and FIG. 6 (discussed below), in certain embodiments, one or more of the RPS deliveries may include a plurality, or a train, of pulses. In certain embodiments, as illustrated, such train of pulses is administered in an alternating manner, such that the pulse train is biphasic. That is, each alternating pulse of the train is of opposite polarity. While it should be appreciated that a monophasic train of pulses could be just as well used with RPS delivery, it may be more favorable to use a biphasic pulse train because doing so enables a reduced build-up of polarization charge. Such a build-up could result in a resistant effect on subsequent administrations of RPS, potentially resulting in a reduction in efficiency.

In embodiments in which RPS is used in place of ICC, or alternatively, in conjunction with other therapies for treating conditions of cardiac dysfunction, e.g., when used with ICC therapy, it should be appreciated that RPS therapy would generally be delivered using different parameters than those of the other therapies. Such delivery parameters can include therapy timing, therapy amplitudes, therapy polarities, and therapy scheduling. In addition, the electrodes for delivering the RPS, in certain embodiments, can be different than those used for administering the other therapies.

Since both the RPS and ICC therapies are similar in that they involve stimulation pulses being administered within the refractory period, the following examples are provided to distinguish therapy parameters for RPS when used in place of ICC, or alternatively, used in conjunction with ICC. As discussed above, with reference to FIG. 5, the timing of the RPS therapy is generally set so as to be delivered almost immediately following a V-EVENT in order to guarantee that RPS is delivered within the ERP, and, when necessary, to allow sufficient modulation of the ERP for subsequent ICC stimulation. The pulse amplitudes of RPS and ICC are generally independently controllable as the RPS therapy has the dual purpose of increasing contractility and modulating the ERP, whereas the ICC therapy is generally used for increasing contractility. However, in certain embodiments, the pulse amplitudes for the RPS therapy can be varied not only to provide this dual purpose, but also to compensate for a lessening in amplitude of ICC stimulation pulses so as further reduce the arrhythmia risk from the ICC. With respect to pulse polarity, RPS, when involving a train of pulses, can be generally administered in a biphasic fashion so as to reduce the build-up of charge (as further described below), while ICC is generally administered in a monophasic manner so as to achieve the desired response from the cardiac tissue. For therapy scheduling, in certain embodiments, RPS may be only periodically used with ICC based on particular heart parameters being sensed e.g., heart rate. For example, RPS may only be used with ICC when high heart rates are observed, which tends to decrease ERP. Finally, in certain embodiments, RV electrodes can be used for delivery of RPS to ensure better cardiac resynchronization, while LV electrodes can be used for delivery of ICC because of increased effectiveness in response for the cardiac tissue.

FIG. 6 illustrates an exemplary timing diagram showing the delivery of RPS during the course of PESP therapy in accordance with certain embodiments of the invention. Similar to FIG. 5, for the sake of simplicity, the PESP therapy pulses are not referenced in FIG. 5; however, it should be appreciated how such pulses may be generally provided for each V-EVENT, as shown in FIG. 5. In accordance with one aspect of embodiments of the invention, RPS delivery is again timed out from each sensed or paced event (e.g., the illustrated V-EVENTs), beginning after the sensed or paced event yet terminating prior to the end of the ERP. Like the RPS administrations shown in FIG. 5, the administrations shown in FIG. 6, in certain embodiments, include one or more pulses, and in certain embodiments, are administered biphasically when administered in a pulse train. In addition, while RPS is shown to occur a somewhat sizable period of time after each of the V-EVENTs, such is again generally shown for clarity to the reader, as the RPS therapy should begin almost immediately after the V-EVENT is sensed, and in certain embodiments, would occur during the V-EVENT, likewise to that already described with respect to FIG. 5.

Similar to that shown in FIG. 5, the RPS stimulation occurs well within the ERF of each sensed or paced event so as not to induce an arrhythmia. As mentioned above, in certain embodiments, one or more parameters of the RPS stimulation may be adjusted periodically in order to modulate the ERP. As described above with reference to FIG. 5, one of these parameters may be pulse amplitude. In summary, by administering pulses of higher amplitude (e.g., from a pre-determined baseline stimulation pulse for the patient) using RPS, one will see a shortening of the ERP almost immediately and within subsequent cycles. As should be appreciated, modulation of the ERP in this manner would be desirable during PESP therapy, where the PESP stimulation pulses need to be delivered within the non-refractory period. In turn, through such EPR modulation (shortening of the EPR), an environment is created where it is easier to position the PESP pulses within the non-refractory period and outside such shortened ERP. In addition, one can further minimize any risk of potentially missing the non-refractory period with the PESP stimulation pulses during such therapy, creating a safer mode of providing PESP therapy. As should also be appreciated, if the ERP is decreased too significantly via RPS, the ERP length can be elongated by decreasing the amplitude of the one or more RPS pulses. Therefore, in certain embodiments, the RPS stimulation can be adjusted continuously so as to "zero in" on the ERP length that is most desired, based on the therapy (e.g., RPS and/or PESP and/or ICC) given.

As described above, by being able to modulate the ERP using RPS, the PESP therapy can be made safer and easier. However, through the use of RPS, more energy is applied accordingly to the heart tissue during the refractory period. Such increased energy generally leads to increased contractility of the corresponding heart tissue, which is one of the goals of PESP therapy. As such, the application of RPS therapy at least leads to dual benefits: enabling manipulation of the ERP and increasing contractility of the heart tissue.

In FIG. 6, in contrast to the RPS therapy shown in FIG. 5, in certain embodiments, there may be more than one RPS administration per cardiac cycle. As described above with respect to PESP therapy, the PESP pulse following the initial V-EVENT results in a coupled pace, or second V-EVENT, within the same cardiac cycle. As such, there is a further depolarization and repolarization of the heart tissue following this coupled pulse. Because of this further repolarization of the heart tissue, there is a further ERP during the same cardiac cycle. In certain embodiments, RSP is delivered during this further ERP as well, not only resulting in increased contractility of the heart tissue, but also enabling one to modulate the further ERP as well, with the ability to dictate the overall duration of the cardiac cycle.

In summary, the RPS can be used to achieve at least two purposes, including the enablement of modulating the ERP and increasing contractility of the heart tissue. While pulse amplitude is provided as one of the parameters that can be adjusted to modulate the ERP, it is to be appreciated that other parameters may alternatively, or in combination, be adjusted in order to modulate the ERP. For example, a few other parameters of the RPS stimulation that could be modified are pulse width, and if the RPS stimulation is a train of pulses, pulse polarity and pulse frequency. With respect to pulse polarity, using the teachings presented by Brunckhorst et al. in their publication dealing with non-excitatory stimulation, herein incorporated by reference in relevant part, each train of RPS pulses may be modified in part with respect to polarity to also modulate the ERP (see Brunckhorst et al., "Cardiac Contractility Modulation by Non-Excitatory Currents: Studies in Isolated Cardiac Muscle", *The European Journal of Heart Failure*, 8. p. 7-15, 2006.). In brief, a pulse train having a portion which is negative or cathodic in part (with respect to polarity), as opposed to the rest of the pulse train, has been observed to shorten the ERP. Conversely, a pulse train having a portion which is positive or anodic in part (with respect to polarity), as opposed to the rest of the pulse train, has been observed to elongate the ERP. In summary, by using a system for ICC and/or PESP therapies that modulates the ERP via RPS by any one or combination of the above fashions, there would be more tolerance of sensing/timing errors and less chance of inducing arrhythmias.

As alluded to above, because the use of RPS enables the modulation of the ERP, one, by using RPS, can also dictate the overall duration of the cardiac cycle, while still increasing contractility. For example, by shortening the cardiac cycle while delivering ICC and/or PESP, or other therapies, the therapies are observed to have increased effectiveness. However, in order to shorten the cardiac cycles using RPS, one must still be able to sufficiently deliver the ICC and/or PESP pulses in their respective refractory and non-refractory regions. As such, the room for error that was alluded to earlier in using ICC and/or PESP is reduced. In turn, there is greater importance in finding the location of the refractory-nonrefractory boundary in the cardiac cycles. Additionally, while FIG. 6 is depicted as illustrating RPS being used in conjunction with PESP therapy, in certain embodiments, ICC and PESP therapies may be both delivered to treat the patient. As such, FIG. 6 would not change; however, there would be a greater need of finding the refractory-nonrefractory boundary in order to make sure that the ICC and PESP stimulation pulses were delivered within the respective refractory and nonrefractory regions of the cardiac cycle.

Many methods of effectively determining the refractory-nonrefractory boundary are known. For example, it is known that the refractory period is closely associated with the Q-T interval, which may be derived from electrogram signals or other physiologic sensor signals by techniques known in the art. The Q-T interval length can be used to estimate the duration of the refractory period either directly, or by incorporating a function of heart rate and sensing delays. In the case of PESP therapy, the Q-T interval length can be estimated by the time interval from an extra systole stimulation pulse to an evoked T wave and would be slightly longer than a Q-T interval length from a cardiac cycle not associated with PESP. This is because the extra depolarization caused by the PESP prolongs the QT interval slightly.

Alternatively, an evoked response of the PESP stimulation could be monitored to indicate whether the PESP therapy was delivered in the refractory period or not. For example, a number of electrical pulses are applied to the myocardium, beginning during the refractory period. The result of each pulse is sensed on an EGM from either the stimulating electrode or an auxiliary electrode until an evoked response is sensed, indicating that the pulse caused an extra systole. At this point, no further pulses would be applied to minimize the risk of inducing arrhythmias.

In another example, a single pulse's amplitude and timing may be manipulated until capture is detected by an evoked R wave. If capture is lost, the stimulus pulse is delayed more, or amplitude increased, or the number of pulses in a PESP pulse train is increased. Also, the characteristics of a pressure waveform (or any other mechanical response variable) used to assess whether the PESP stimulation is/was capturing the ventricles can be utilized when practicing embodiments of the invention. The presence of the extra systole could be identified by a small ventricular pressure pulse 5-80% of the size of the preceding pressure pulse or through a suitable algorithm such as a template-matching algorithm. A transition between capture and noncapture for a pulse intended to serve as an extrasystole may also be identified by a change in the pressure waveform of the subsequent potentiated beat. This can be clearly illustrated with respect to the arterial pulse pressure.

Further, optional ICC may be delivered using a waveform including one or more pulses during the refractory period. To ensure that the ICC stimulation does not enter the vulnerable period, the length of the refractory period is estimated using the mechanisms discussed above. If ICC is exclusively intended, then detection of an extra systole should result in a reduction of the stimulus delay time, amplitude, or pulse number.

It should be appreciated that the above methods involve making an estimate of the refractory-nonrefractory boundary. Once such estimate is determined, in particular with respect to PESP therapy, the extra-stimulus interval (ESI) can be set. ESI is the period of time measured between the start of a V-EVENT and the start of the next consecutive V-EVENT, generally including both the refractory and nonrefractory periods for the prior V-EVENT. As such, once the ESI is set, the system would be able to deliver the PESP pulses safely within the nonrefractory period of the ESI and in turn, minimize the cardiac cycle accordingly. As the refractory-nonrefractory boundary is very important and varies from patient to patient and even with a patient over time, with disease and drugs, these methods may be employed periodically or continually to a stimulation timing algorithm portion of the device in order to adjust the ESI as needed, as is described in more detail in U.S. patent application Ser. No. 10/680,528, filed Oct. 7, 2003 by Deno et al. (US 2005/0075676 A1, published Apr. 7, 2005), herein incorporated by reference in relevant part.

Figure 7:
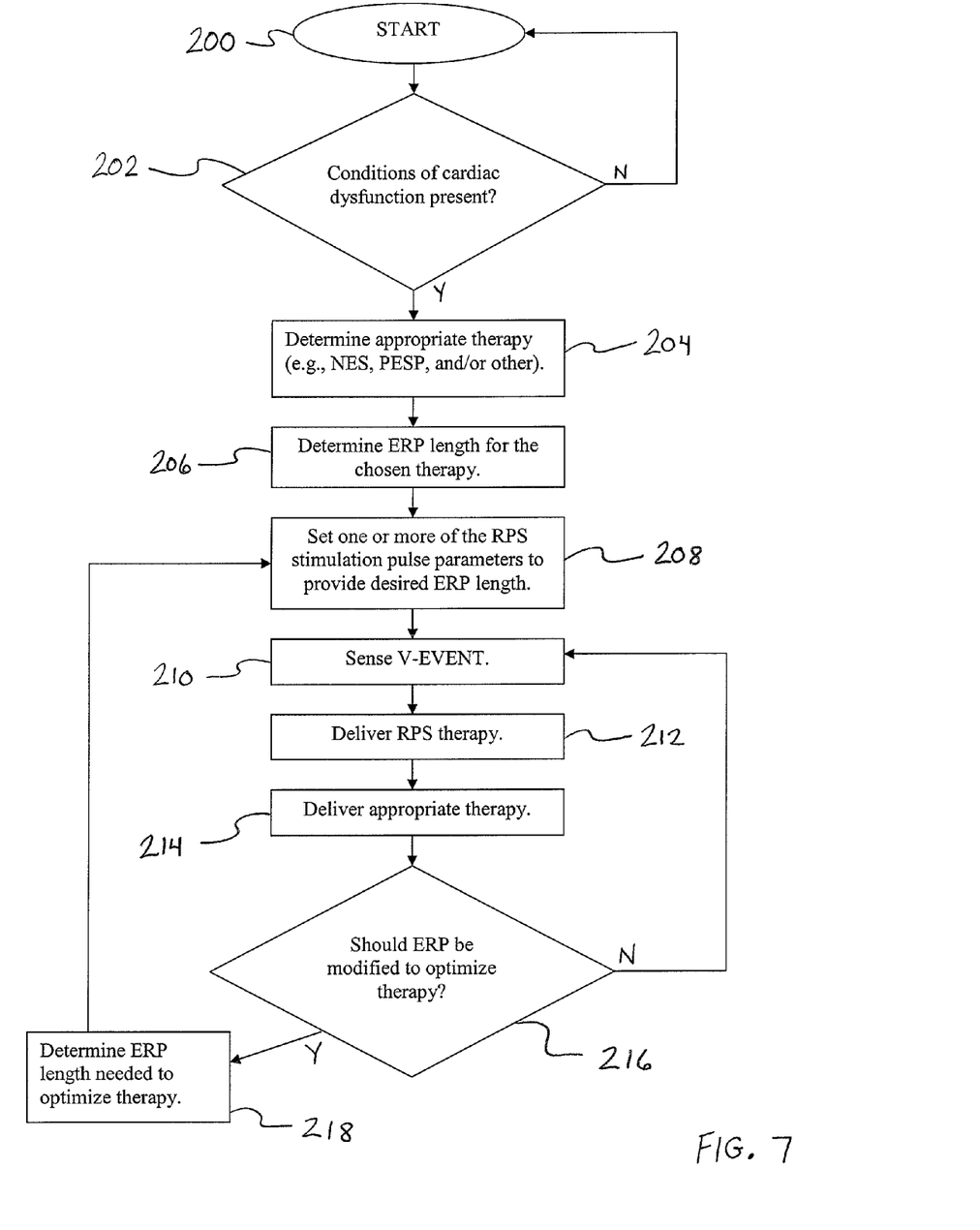
FIG. 7 is a flowchart of a method of using RPS in accordance with certain embodiments of the invention.

FIG. 7 illustrates a flowchart of a method of using RPS in accordance with certain embodiments of the invention. In certain embodiments, the method can be performed by any medical device used to treat cardiac dysfunction conditions, including heart failure. Step 200 of the method is generally a pre-therapy stage, in which there is a monitoring of the cardiac parameters of the patient by use of one or more implanted sensors of the medical device. Step 202 involves the transfer of the cardiac parameters from the sensors to a processor of the medical device. In this step, a determination is made as to whether conditions of cardiac dysfunction are present. If there are no such conditions present, the method simply reverts back to monitoring the cardiac parameters in step 200. However, if one or more conditions are found to be present, a determination is made by the processor in step 204 as to the most appropriate therapy in treating the conditions. As discussed herein, the appropriate therapy may be ICC, PESP, pacing, or other therapies. Alternatively, the appropriate therapy may be a combination of these therapies.

Once the appropriate therapy is chosen, a determination is made in step 206 as to whether the ERP length should be modulated. Reasons for modulating the ERP length are discussed herein, and would include enabling delivery of the therapy to be safer, easier, and/or enabling the therapy, once delivered, to be more effective. Assuming a decision is made to modulate the ERP length, the ERP length is then determined in step 206 based on the chosen therapy. For example, as mentioned herein, one may favor an elongated ERP for ICC therapy, while favoring a shortened ERP for PESP therapy. Accordingly, in step 208, one or more of the parameters of the RPS therapy stimulation pulses would be set to, in turn, provide the desired modulation of the ERP. As mentioned herein, these parameters may include amplitude, duration, and frequency. Once the RPS parameters are set, a sensed V-EVENT in step 210 will trigger the therapies to be delivered. In turn, the RPS therapy is delivered in step 212 and the chosen therapy is delivered thereafter in step 214.

Step 216 involves a determination being made as to whether the ERP should be further modified to optimize the chosen therapy. As described herein, by modulating the ERP, one not only can provide a greater degree of ease and safety in delivering the therapy, but one can also affect the cardiac cycle length as well, which can have a direct impact on the overall effectiveness of the therapy. As such, in certain embodiments, the processor of the medical device may be designed to automatically adjust the ERP (e.g., using capture detection as described above) to, in turn, affect the cardiac cycle length, and as a result, optimize the therapy. Additionally, due to changes in the patient's condition or other factors that may impact the therapy, one may also need to modify the ERP based on change in therapy parameters. In turn, such situations would also fall under step 216. If a determination is made to further modify the ERP, step 218 involves determining the ERP length needed to optimize the therapy. Step 218 loops back to step 208, where one or more of the RPS therapy stimulation pulse parameters once again need to be set to provide the new ERP length. If, however, a determination is made that the ERP does not need to be modified, step 218 loops back to step 210, wherein the next V-EVENT is being ascertained.

There are a multitude of situations in which delivery of RPS, according to one or more of the above described embodiments, may be applicable. For example, when providing ICC, PESP, and/or other therapies for treating cardiac dysfunction, stimulation lead location may exhibit delayed local conduction and increased latency. As such, there is a delay in the effective ESI in adjacent heart tissue, reducing the effectiveness of the therapy, e.g., PESP and/or CRT (cardiac resynchronization therapy). By utilizing RPS using the above teachings, the local refractory period can be shortened (e.g., by employing higher amplitude and/or more frequent RPS pulses in the refractory period) so as to help alleviate the local conduction and latency problems.

Another example could involve such therapies being delivered where the cardiac tissue adjacent to the stimulation electrode location has a longer ERP, leading to a prolonged period of depolarization spread over the majority of the heart. In turn, this may result in reduced effectiveness of the therapy (e.g., PESP and/or CRT). By utilizing RPS using the above teachings, the local refractory period can be shortened (e.g., by employing higher amplitude and/or more frequent RPS pulses in the refractory period) so as to help alleviate the depolarization concerns.

A further example could involve such therapies being delivered where there are prolonged global refractory periods, which while not resulting in dysynchrony per se, may be resulting in reduced potentiation and less effective therapy (e.g., PESP). By utilizing RPS using the above teachings with multiple stimulation electrodes, the global refractory period can be shortened (e.g., by employing higher amplitude and/or more frequent RPS pulses in the refractory periods of each of the electrodes) so as to enable the shortening of global ESI and thus, enhanced potentiation.

One additional example could solely involve CRT therapy, which may benefit from a more globally coordinated depolarization and contraction. By utilizing RPS with CRT using the above teachings, the local refractory period can be modulated as necessary with respect to the ventricles so as to help re-coordinate the action of the right and left ventricles.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A medical device for treating cardiac dysfunction, comprising:
   implantable sensor means for obtaining one or more cardiac parameters of a patient;
   a processor means for processing the one or more cardiac parameters to determine whether cardiac dysfunction is present;
   therapy delivery means for delivering therapies upon a determination of cardiac dysfunction being present, the delivered therapies comprising both stimulation of excitable tissue to treat the cardiac dysfunction and modulation of the excitable tissue's effective refractory periods to achieve a desired effective refractory period; and
   wherein the stimulation to treat the cardiac dysfunction comprises post extrasystolic potentiation, and wherein the refractory period modulation comprises refractory period stimulation shortening of one or more of an initial refractory period and a secondary refractory period.

2. A medical device according to claim 1, wherein the medical device comprises one or more of diagnostic monitoring equipment, an external medical device system, an implantable hemodynamic monitor, an implantable cardioverter-defibrillator, a cardiac pacemaker, a cardiac resynchronization therapy pacing device, and a drug delivery device.

3. A medical device according to claim 1, wherein the implantable sensor means comprise one or more of sense/pace electrodes, blood pressure sensors, accelerometers, impedance electrodes, flow probes, microphones, sonometric crystals, metabolic sensors, and chemical sensors.

4. A medical device according to claim 1, wherein the refractory period stimulation comprises a plurality of stimulation pulses, and wherein the plurality of stimulation pulses has a biphasic arrangement.

5. A medical device according to claim 1, wherein the stimulation to treat the cardiac dysfunction comprises delivery of a first one or more pulses and wherein the refractory period stimulation comprises delivery of a second one or more pulses having an adjustment to one or more of amplitude, duration, and frequency of the first one or more stimulation pulses.

6. A medical device according to claim 1, wherein the refractory period stimulation comprises shortening of both the initial refractory period and the secondary refractory period of the cardiac cycle.

7. A medical device according to claim 1,
wherein stimulation pulses of the refractory period stimulation have one or more of a higher amplitude, a higher duration, a lower polarity in part, and a higher frequency than stimulation pulses of the stimulation to treat the cardiac dysfunction.

8. A medical device for treating cardiac dysfunction, comprising:
implantable sensor means for obtaining one or more cardiac parameters of a patient;
a processor means for processing the one or more cardiac parameters to determine whether cardiac dysfunction is present;
therapy delivery means for delivering therapies upon a determination of cardiac dysfunction being present, the delivered therapies comprising;
non-excitory stimulation comprising delivery of a first one or more stimulation pulses to excitable tissue to treat the cardiac dysfunction; and
refractory period stimulation comprising delivery of a second one or more stimulation pulses to elongate the effective refractory period of the excitable tissue and
wherein the second one or more stimulation pulses have one or more of a lower amplitude, a lower duration, a higher polarity in part, and a lower frequency than that contained in the first one or more stimulation pulses.

* * * * *